(12) United States Patent
Traxler et al.

(10) Patent No.: US 6,623,689 B2
(45) Date of Patent: Sep. 23, 2003

(54) BALLOON WRAP DEVICE AND METHOD

(75) Inventors: Richard J. Traxler, Minneapolis, MN (US); Brent C. Gerberding, Minneapolis, MN (US); Scott E. Arndt, St. Michael, MN (US); Tracee E. J. Eidenschink, Wayzata, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 286 days.

(21) Appl. No.: 09/907,235

(22) Filed: Jul. 17, 2001

(65) Prior Publication Data

US 2001/0047149 A1 Nov. 29, 2001

Related U.S. Application Data

(62) Division of application No. 09/034,452, filed on Mar. 4, 1998, now Pat. No. 6,283,743.

(51) Int. Cl.[7] ............................................. B29D 22/00
(52) U.S. Cl. ...................................................... 264/573
(58) Field of Search ........................................ 264/573

(56) References Cited

U.S. PATENT DOCUMENTS

| | | |
|---|---|---|
| 4,444,186 A | 4/1984 | Wolvek et al. |
| 4,681,092 A | 7/1987 | Cho et al. |
| 4,901,707 A | 2/1990 | Schiff |
| 4,930,341 A | 6/1990 | Euteneuer |
| 5,015,230 A | 5/1991 | Martin et al. |
| 5,015,231 A | 5/1991 | Keith et al. |
| 5,041,125 A | 8/1991 | Montano, Jr. |
| 5,053,007 A | 10/1991 | Euteneuer |
| 5,087,246 A | 2/1992 | Smith |
| 5,147,302 A | 9/1992 | Euteneuer et al. |
| 5,209,799 A | 5/1993 | Vigil |
| 5,226,880 A | 7/1993 | Martin |
| 5,342,570 A | 8/1994 | Ledoux et al. |
| 5,350,361 A | 9/1994 | Tsukashima et al. |
| 5,352,236 A | 10/1994 | Jung et al. |
| 5,783,227 A | 7/1998 | Dunham |
| 5,836,952 A | 11/1998 | Davis et al. |
| 5,911,452 A | 6/1999 | Yan |
| 6,283,743 B1 | 9/2001 | Traxler et al. |

*Primary Examiner*—Suzanne E. McDowell
(74) *Attorney, Agent, or Firm*—Crompton, Seager & Tufte, LLC

(57) ABSTRACT

Method and apparatus for sequentially forming, wrapping and compressing a catheter balloon either during the initial manufacturing process or after a medical procedure. The balloon may be formed, wrapped and compressed by simply advancing the balloon through a balloon wrapping tool and selectively inflating and deflating the balloon therein. The balloon wrapping tool preferably includes a flap forming bore, a flap wrapping bore and a flap compression bore which form, wrap and compress the balloon, respectively, when the balloon is advanced therethrough.

5 Claims, 4 Drawing Sheets

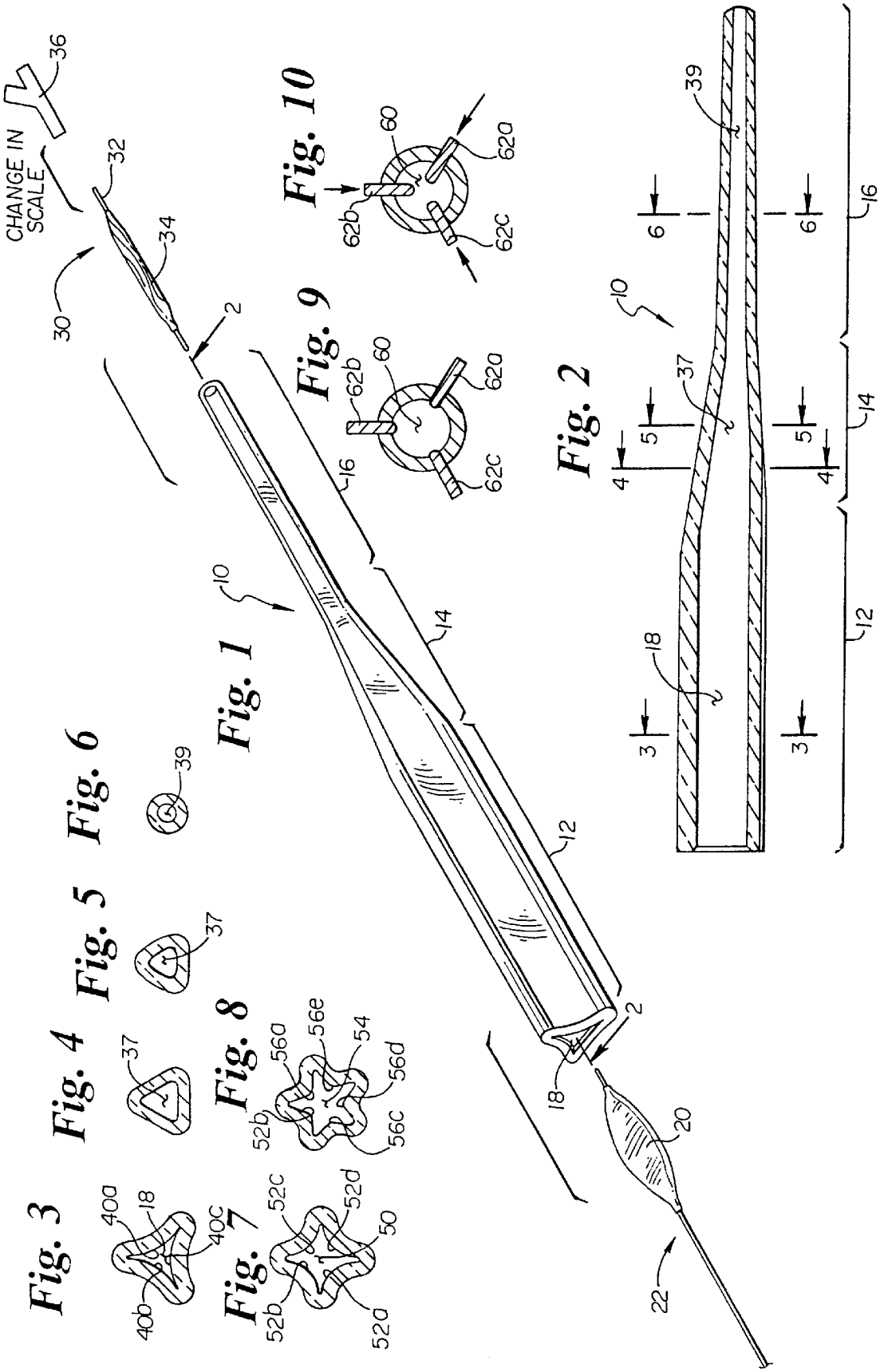

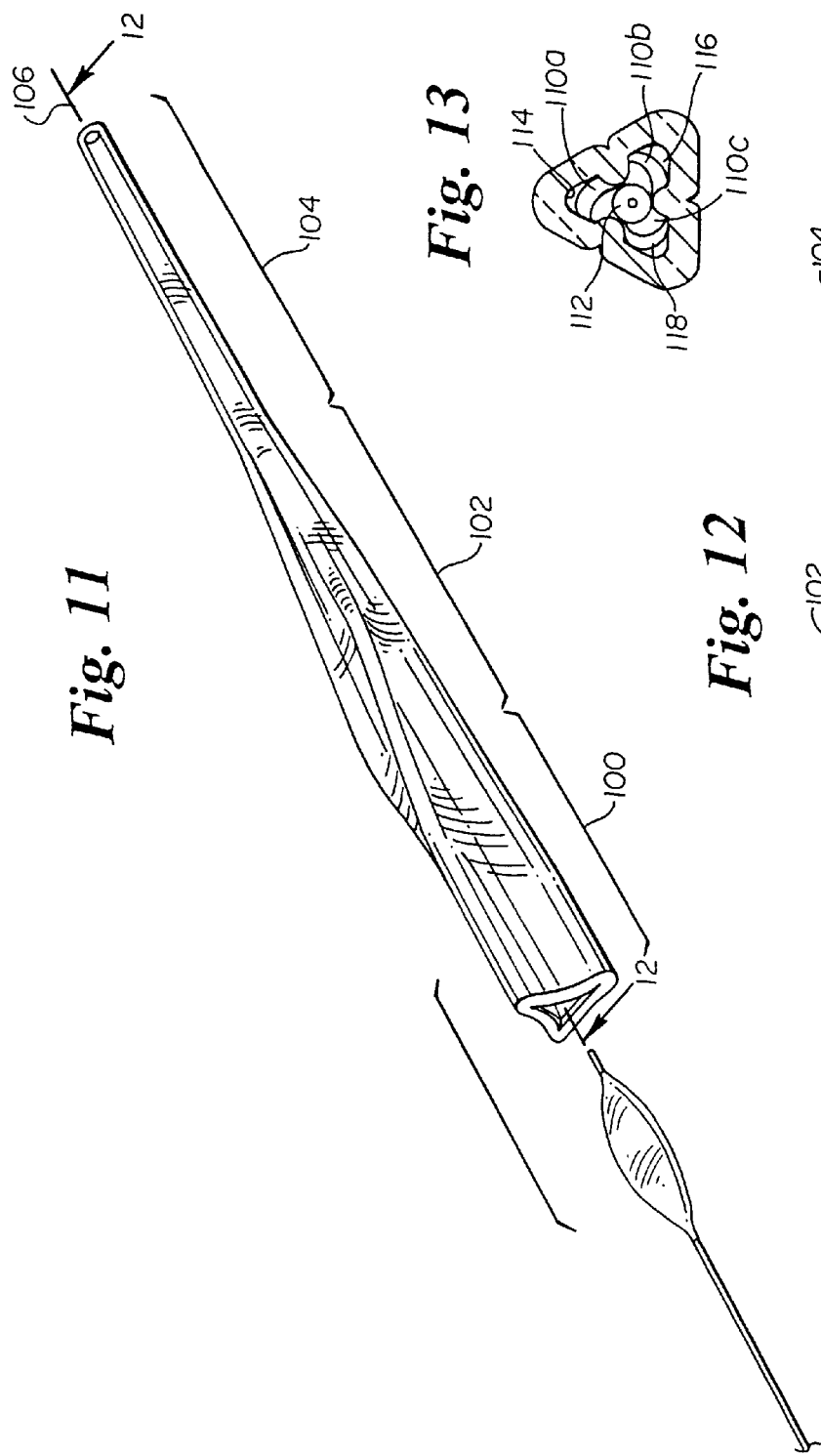
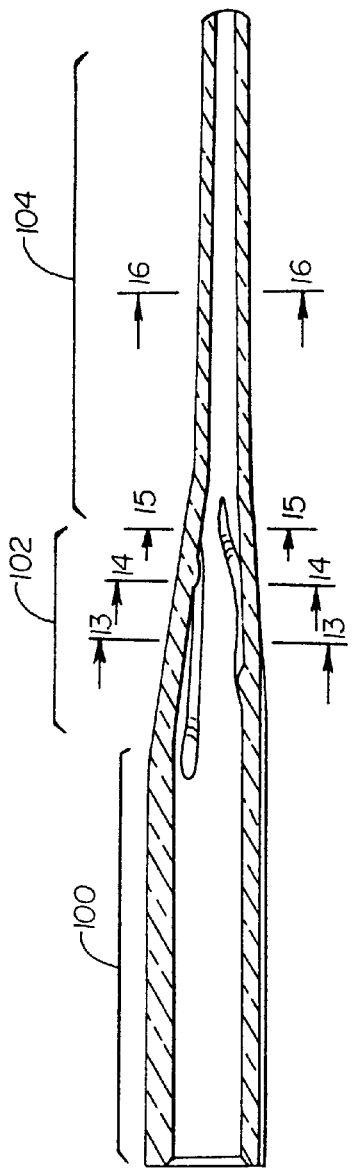

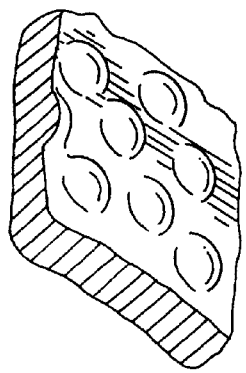
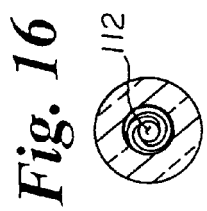
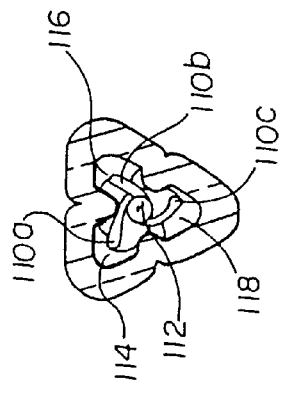
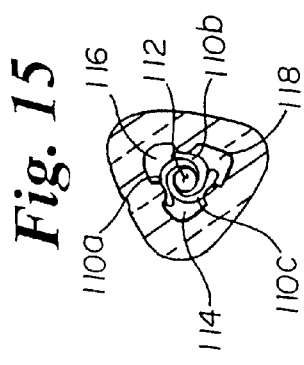
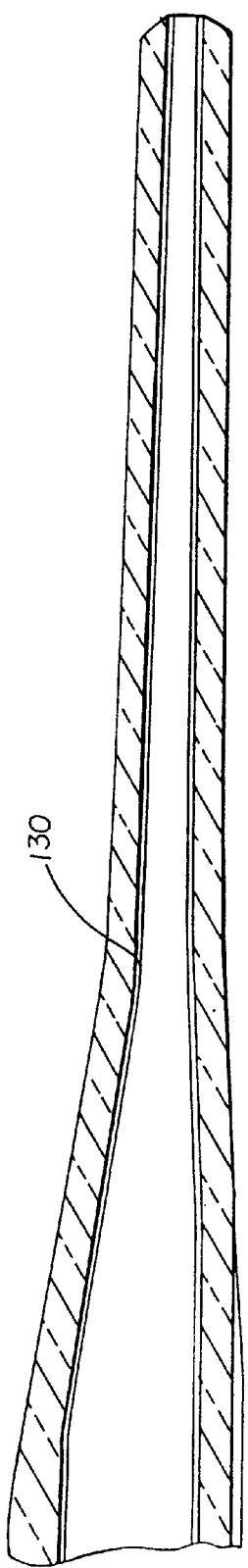

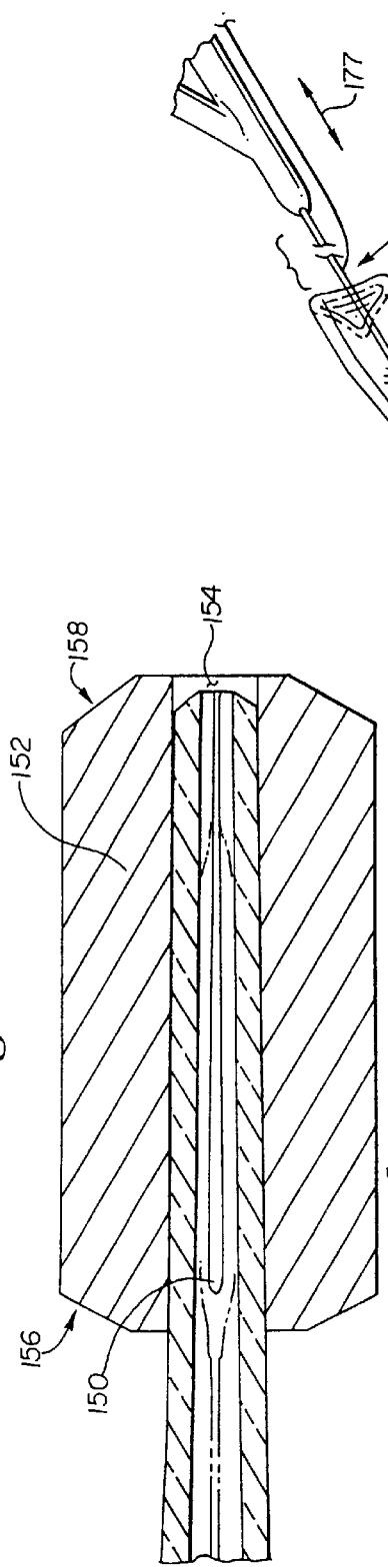
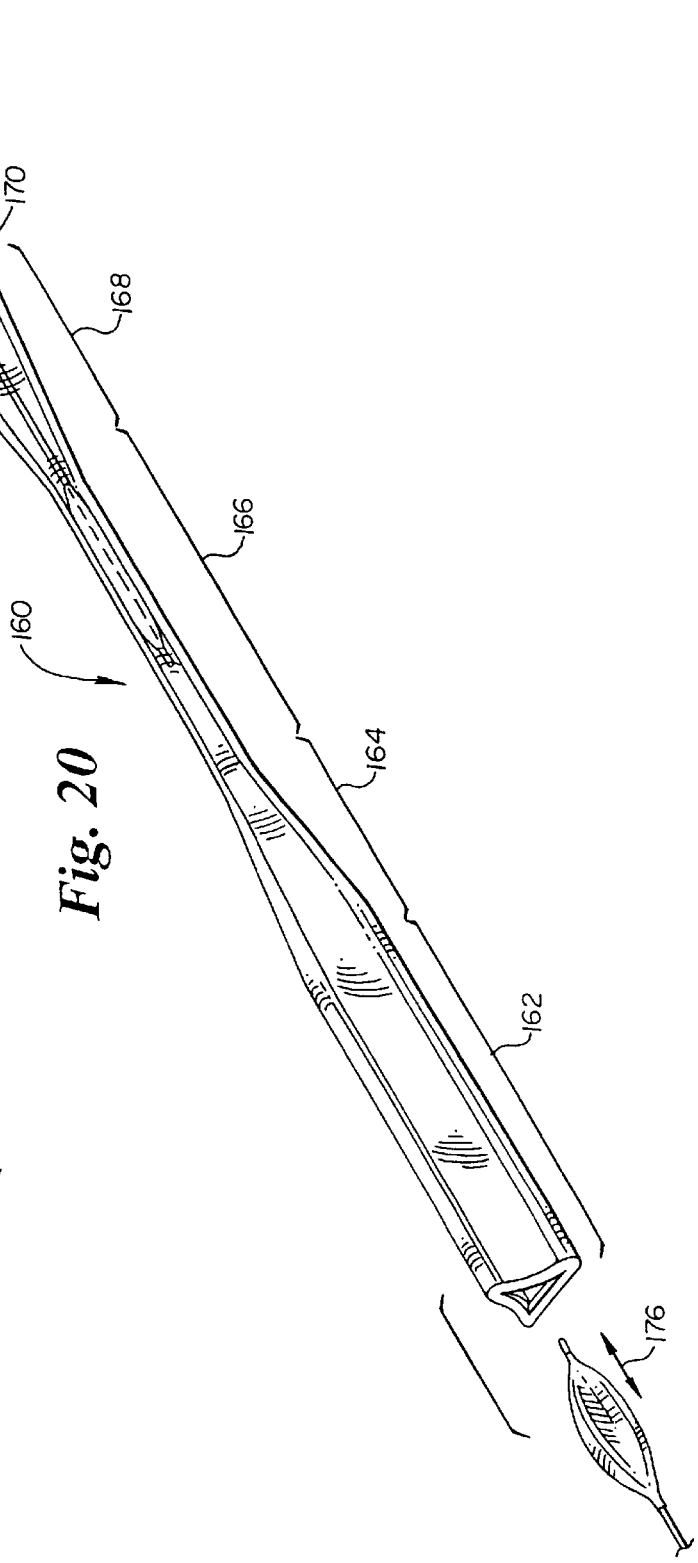

BALLOON WRAP DEVICE AND METHOD

This application is a divisional of U.S. application Ser. No. 09/034,452, filed on Mar. 4, 1998, now U.S. Pat. No. 6,283,743.

FIELD OF THE INVENTION

The present application is related to balloon type catheter devices, and more particularly to a method and apparatus for forming, wrapping and compressing balloons to provide a reduced profile catheter configuration.

BACKGROUND OF THE INVENTION

Angioplasty has gained wide acceptance in recent years as an efficient and effective method for opening stenosis in the coronary arteries and in other parts of the vascular system. The most widely used form of angioplasty makes use of a dilatation catheter which has an inflatable balloon at its distal end. Using fluoroscopy, the physician guides the catheter through the vascular system until the balloon is positioned across the stenosis. The balloon is then inflated by supplying a fluid under pressure through an inflation lumen to the balloon. The inflation of the balloon causes stretching of the artery and pressing of the lesion into the artery wall to reestablish acceptable blood flow through the artery.

Intra-aortic balloon catheters have also gained wide acceptance in recent years. Intra-aortic balloon catheters are typically inserted into the aorta of the heart, often percutaneously, and then inflated and deflated out of phase with the natural pumping action of the heart. By doing so, the intra-aortic balloon catheters can supplement the natural pumping action of the heart. Both dilatation catheters and intra-aortic balloon catheters are balloon type catheters devices.

One important characteristic of balloon type catheters is the distal "profile", which is determined by the outer diameter of the distal end portion of the balloon when deflated. This outer diameter affects the ease and ability of the catheter to pass through a guide catheter, through the coronary arteries and/or across a tight lesion. Considerable effort has been spent in developing low profile balloon type catheters by minimizing the dimensions of the core or inner tube which extends through the balloon to its distal end, and by reducing the wall thickness, to the extent possible, of the balloon itself.

A complicating factor in minimizing the deflated profile of a catheter balloon is that the balloon membrane is often not distensible, i.e. it does not stretch or contract in response to changes in internal pressure. This is typically true for both dilatation catheters and intra-aortic balloon type catheters. Thus, the balloon membrane typically has a constant surface area regardless of whether the balloon is inflated or deflated. To reduce the outer diameter of the balloon catheter in its deflated condition, it is common to fold the balloon flat, so that two wings are brought together in some fashion, as by folding or wrapping, so as to reduce the overall diameter of the deflated balloon. In use, the inflation fluid that is applied to the folded balloon causes the flaps to unwrap so that the balloon can inflate to its full inflated state.

While it is desirable to minimize the profile of the catheter, it is also desirable to provide a large inflated outer diameter to the balloon. As the inflated outer diameter is made larger, the flaps of the balloon become relatively large relative to the core or inner tube of the catheter. The result is that it is often difficult to eliminate the interstitial space between the flaps when folded together or wrapped around the catheter.

Various methods and balloon configurations have been proposed in the prior art for providing a balloon type catheter that has the lowest profile possible when deflated and the largest possible diameter when inflated. One approach, which is suggested, for example, in U.S. Pat. No. 5,087,246 to Smith and in U.S. Pat. No. 5,147,302 to Euteneuer et al., is to provide a dilatation balloon having more than two flaps or wings (for example, three wings) such that when the flaps or wings are wrapped circumferentially, the distance that each flap extends around the catheter is reduced when compared with the two flap configuration. The ease with which such flaps fold is also enhanced when the number is increased, such that when the balloon is deflated and withdrawn through the guide catheter following a procedure, the balloon more readily returns to its wrapped condition. The result is a reduced deflated profile given the same inflated diameter.

Typically, the balloon flaps are formed during the manufacturing process of the catheter. U.S. Pat. No. 5,350,361 to Tsukashima et al. discloses a method for preparing a tri-fold balloon configuration. Tsukashima et al. initially impart the tri-fold configuration to the balloon by inflating the balloon in a longitudinal interstitial channel defined by three substantially cylindrical pins arranged in a pyramid-type stack. While the balloon is secured in this channel, negative pressure is applied to an inflation lumen of the balloon to deflate the balloon, thus providing the tri-fold configuration to the balloon.

The balloon may be "heat set" in the desired fold configuration so that the balloon returns to the fold configuration when the balloon is deflated. Tsukashima et al. suggest heating the creases defined by the three tri-fold flaps with a longitudinal heating element. This apparently softens the balloon material in the longitudinal creases, so that the same creases will tend to form whenever the balloon is deflated.

Once the flaps are formed and/or set in the balloon, it is common to manually fold the balloon flaps circumferentially around the catheter. The flaps are then typically held in place with a balloon protector. A balloon protector typically serves two functions. First, the balloon protector protects the balloon and the distal tip of the catheter from possible damage during shipping. Second, the balloon protector wraps the balloon tightly in its deflated condition to minimize the outer diameter of the balloon in its deflated state.

A typical balloon protector is applied to the distal end portion of the catheter prior to packaging and sterilization of the catheter. The sterilization process often involves exposing the catheter, with the balloon protector in place, to an elevated temperature for a predetermined time period. With certain balloon materials, such as polyolefin, the sterilization process causes the balloon to be "heat set" in the folded or wrapped condition in which it is held by the balloon protector. As a result, when the balloon protector is later removed, the balloon tends to remain in the tightly wrapped condition.

To further reduce the profile of the wrapped balloon, the balloon protector can be constructed to be radially compressible. This further reduces the interstitial space in the wrapped balloon particularly during the heat setting process. Thus, when a balloon material is used that exhibits heat set characteristics, the deflated balloon will tend to remain tightly compressed even after removal of the balloon protector.

While the prior art provides some improvement in the field of folding, wrapping and compressing balloon type catheters, there are still a number of limitations, some of which are discussed below. One limitation is that the prior art balloon flaps are typically manually folded over the catheter by an operator during the manufacturing process. This can be a relatively slow and tedious process, and the quality of the wrap is often dependent on the skill of the operator. Second, the balloon protector must typically be installed over the wrapped balloon, which can also be a slow and tedious process. It would be desirable, therefore, to provide an apparatus and method that helps form, wrap and compress the balloon flaps during the manufacturing process.

It would also be desirable to provide a tool that could be used by a physician during a medical procedure to reform the flaps and rewrap the balloon. It has been found that once a balloon has been inflated to relatively high inflation pressures, the balloon material can loose the heat set characteristics provided during the manufacturing process. For example, a tri-fold balloon that has been inflated to relatively high pressures (10–15 atm) may take on a pancake shape having, for example, only two flaps when deflated. Further, the balloon may not return to the original low profile wrap configuration. This can prohibit the crossing of additional lesions using the same catheter. To reach other lesions, the physician must often withdraw and discarded the catheter in favor of a new catheter that has a balloon that was tightly wrapped during the manufacturing process.

SUMMARY OF THE INVENTION

The present invention overcomes many of the disadvantages of the prior art by providing a method and apparatus for sequentially forming, wrapping and compressing a catheter balloon during the initial manufacturing process and/or during a subsequent medical procedure. In either case, the balloon may be formed, wrapped and compressed by simply advancing the balloon through a balloon wrapping tool, and selectively inflating and deflating the balloon therein according to the methods described below.

In one illustrative embodiment of the present invention, the balloon wrapping tool includes a flap forming section, a flap wrapping section and a flap compression section. The flap forming section has a flap forming bore extending therethrough that is shaped to produce at least two flaps in the balloon when the balloon is inflated and subsequently deflated therein. The flap wrapping section, which is preferably positioned adjacent to the flap forming section, has a flap wrapping bore extending therethrough that is axially aligned with the flap forming bore and shaped to wrap the at least two flaps around the catheter as the deflated balloon is advanced therethrough. The flap compression section is preferably positioned adjacent to the flap wrapping section, and includes a flap compression bore extending therethrough. The flap compression bore is preferably axially aligned with the flap wrapping bore to receive the wrapped balloon. The wrapped balloon may be inflated and deflated in the flap compression bore to compress the wrapped balloon and to set the creases therein.

An illustrative method of the present invention includes the steps of: inflating the balloon in the flap forming bore; deflating the balloon in the flap forming bore to produce the at least two flaps in the balloon; and advancing the deflated balloon into the flap wrapping bore to wrap the at least two flaps around the catheter as the deflated balloon is advanced therethrough to provide a wrapped balloon. The illustrative method may further include the steps of: advancing the wrapped balloon into the flap compression bore; inflating the wrapped balloon while in the flap compression bore; deflating the wrapped balloon while in the flap compression bore; and removing the wrapped balloon from the flap compression bore.

In one illustrative embodiment of the present invention, the balloon wrapping tool is initially separated from the catheter, and advanced in a proximal direction over the distal end of the balloon. In this embodiment, the flap forming section is proximal of the flap wrapping section, and the flap wrapping section is proximal of the flap compression section. Once the balloon is positioned in the flap forming section, the balloon is inflated and deflated, as described above. The balloon wrapping tool is then advanced proximally until the balloon is in the flap wrapping section, and finally in the flap compression section. Once the balloon is successfully formed, wrapped and compressed, the balloon wrapping tool is slid distally off the distal end of the catheter.

In another illustrative embodiment, the balloon wrapping tool is advanced in a distal direction over the balloon. In this embodiment, the balloon wrapping tool is preferably provided in a coaxial arrangement with the catheter shaft, and releasably secured to the manifold of the catheter. Accordingly, the flap forming section is positioned distal of the flap wrapping section, and the flap wrapping section is positioned distal of the flap compression section. In this configuration, and after the balloon has been inflated during a medical procedure and subsequently withdrawn proximally from the body, the balloon wrapping tool is released from the manifold and advanced distally over the catheter shaft until the flap forming section of the balloon wrapping tool is positioned over the balloon. The balloon is then inflated and deflated to form the desired flap configuration in the balloon. The balloon wrapping tool is then advanced distally until the balloon is provided in the flap wrapping section, and finally in the flap compression section. Once the balloon is successfully formed, wrapped and compressed, as described above, the balloon wrapping tool may be slid off the distal end of the catheter and discarded.

In another illustrative embodiment of the present invention, the balloon wrapping tool includes, from the proximal end to the distal end, a flap forming section, a flap wrapping section, a flap compression section and another flap wrapping section. As described more fully below, this illustrative embodiment may be particularly useful for wrapping and/or rewrapping the balloon of single operator exchange type device. In a single operator exchange type device, the guide wire typically only extends from a proximal guide wire port, through the balloon, to a distal guide wire port. The proximal guide wire port is typically located just proximal of the proximal end of the balloon. It is known that the guide wire typically provides significant column support for the catheter shaft. Since the guide wire only extends through a distal portion of the single operator exchange type device, the catheter shaft just proximal of the proximal guide wire port may have a reduced column support.

To properly form the balloon, the flap forming section of the balloon wrapping tool preferably has a length that is at least as long as the balloon. When the balloon is advanced into the flap forming section or the compression section, the operator or physician may not be able to grasp the catheter near the proximal guide wire port. Because of the lack of column support, and the inability of the operator or physician to grasp the catheter sufficiently close to the proximal guide wire port, it may not be possible to advance the balloon of a single operator exchange type device into the flap wrapping section and/or flap compression section, as described above.

Accordingly, after the balloon is inflated and deflated in the flap forming section, the balloon may be withdrawn from the balloon wrapping tool. The balloon may then be inserted into the second flap wrapping section, which in this embodiment, is located on the opposite side of the compression section from the flap forming section. Alternatively, the flap wrapping section can be adjacent to the other sections. Since no flap forming section is provided adjacent to the second flap wrapping section, the operator or physician may grasp the catheter shaft near the proximal guide wire port, and provide the needed column support. Thus, the operator or physician may advance the balloon into the second flap wrapping section and the flap compression section to complete the forming, wrapping and compression of the balloon.

BRIEF DESCRIPTION OF THE DRAWINGS

FIG. 1 is a perspective view of a first illustrative balloon wrapping tool in accordance with the present invention;

FIG. 2 is a cross-sectional side view of the balloon wrapping tool of FIG. 1, taken along line 2—2;

FIG. 3 is a cross-sectional view of the balloon wrapping tool of FIG. 2, taken along line 3—3 FIG. 4 is a cross-sectional view of the balloon wrapping tool of FIG. 2, taken along line 4—4;

FIG. 5 is a cross-sectional view of the balloon wrapping tool of FIG. 2, taken along line 5—5 FIG. 6 is a cross-sectional view of the balloon wrapping tool of FIG. 2, taken along line 6—6;

FIG. 7 is a cross-sectional view of the flap forming section of another illustrative balloon wrapping tool for forming four balloon wings;

FIG. 8 is a cross-sectional view of the flap forming section of another illustrative balloon wrapping tool for forming five balloon wings;

FIG. 9 is a cross-sectional view of the flap forming section of yet another illustrative balloon wrapping tool including three movable members;

FIG. 10 is a cross-sectional view of the flap forming section of the illustrative balloon wrapping tool of FIG. 9, with the three movable members extending inwardly;

FIG. 11 is a perspective view of another illustrative balloon wrapping tool in accordance with the present invention having a spiral configuration;

FIG. 12 is a cross-sectional side view of the balloon wrapping tool of FIG. 11, taken along line 12—12;

FIG. 13 is a cross-sectional view of the balloon wrapping tool of FIG. 12, taken along line 13—13;

FIG. 14 is a cross-sectional view of the balloon wrapping tool of FIG. 12, taken along line 14—14;

FIG. 15 is a cross-sectional view of the balloon wrapping tool of FIG. 12, taken along line 15—15;

FIG. 16 is a cross-sectional view of the balloon wrapping tool of FIG. 12, taken along line 16—16;

FIG. 17 is a cross-sectional side view of a balloon wrapping tool that includes a lubricious coating on the inside surface thereof;

FIG. 18 is a cut-away view of an illustrative inner surface of yet another illustrative balloon wrapping tool;

FIG. 19 is a partial cross-sectional side view of the compression section of another illustrative balloon wrapping tool;

FIG. 20 is a perspective view of yet another illustrative balloon wrapping tool in accordance with the present invention.

DETAILED DESCRIPTION OF THE PREFERRED EMBODIMENTS

Referring to FIG. 1, a first illustrative balloon wrapping tool is generally shown at 10. The balloon wrapping tool 10 includes a flap forming section 12, a flap wrapping section 14 and a flap compression section 16. The flap forming section 12 has a flap forming bore 18 extending therethrough that is shaped to produce at least two flaps in the balloon when the balloon is inflated and subsequently deflated therein. The flap wrapping section 14, which is preferably positioned adjacent to the flap forming section 12 as shown, has a flap wrapping bore extending therethrough that is axially aligned with the flap forming bore 18. The flap wrapping bore is shaped to wrap the at least two flaps around the catheter as the deflated balloon is advanced therethrough. The flap compression section 16 is preferably positioned adjacent to the flap wrapping section 14, and includes a flap compression bore extending therethrough. The flap compression bore is preferably axially aligned with the flap wrapping bore to receive the wrapped balloon. The wrapped balloon may be inflated and deflated in the flap compression bore to compress the wrapped balloon and to set the creases therein.

An illustrative method of the present invention includes the steps of: inflating the balloon 20 of a catheter 22 in the flap forming bore 18 to preferably about eight atmospheres for five seconds (this pressure may vary depending on balloon material and other conditions); deflating the balloon 20 in the flap forming bore 18 to produce the at least two flaps in the balloon 20; and advancing the deflated balloon 20 into the flap wrapping bore of the flap wrapping section 14 to wrap the at least two flaps around the catheter as the deflated balloon 20 is advanced therethrough to provide a wrapped balloon. The illustrative method may further include the steps of: advancing the wrapped balloon 20 into the flap compression bore of the flap compression section 16; inflating the wrapped balloon 20 while in the flap compression bore to preferably about 3–5 atmospheres for five seconds; deflating the wrapped balloon 20 while in the flap compression bore; and removing the wrapped balloon 20 from the flap compression bore. Finally, to facilitate the advancement of the catheter through the balloon wrapping tool 10, it is contemplated that a mandrel or guide wire may first be positioned through the balloon wrapping tool 10, and the catheter may be back-loaded over the mandrel. The mandrel provides additional column support to the catheter thereby increasing the pushability of the catheter.

In one illustrative embodiment of the present invention, the balloon wrapping tool 10 is initially separated from the catheter 22, and advanced in a proximal direction over the distal end of the balloon 20. In this embodiment, the flap forming section 12 is proximal of the flap wrapping section 14, and the flap wrapping section 14 is proximal of the flap compression section 16. Once the balloon is positioned in the flap forming section 12, the balloon is inflated and deflated, as described above. The balloon wrapping tool is then advanced proximally, relative to the catheter 20, until the balloon 20 is in the flap wrapping section 14, and finally in the flap compression section 16. Once the balloon is successfully formed, wrapped and compressed, the balloon wrapping tool 10 is slid distally off the distal end of the catheter 22.

In another illustrative embodiment, the balloon wrapping tool 10 is advanced in a distal direction down the shaft of the catheter and over the balloon. In accordance with this embodiment, and referring to FIG. 1, the balloon wrapping tool 10 can be provided in a coaxial arrangement with a catheter shaft 32, and releasably secured to a manifold 36 of the catheter 30. The flap forming section 12 is positioned distal of the flap wrapping section 14, and the flap wrapping section 14 is positioned distal of the flap compression section 16 relative to the catheter 30. In this configuration, and after the balloon 34 has been inflated during a medical procedure and subsequently withdrawn proximally from the body, the balloon wrapping tool 10 is released from the manifold 36 of the catheter 30 and advanced distally over the catheter shaft 32 until the flap forming section 12 of the balloon wrapping tool 10 is positioned over the balloon 34. The balloon 34 is then inflated and deflated to form the desired flap configuration in the balloon 34. The balloon wrapping tool 10 is then advanced distally until the balloon 34 is provided in the flap wrapping section 14, and finally in the flap compression section 16. Once the balloon is successfully formed, wrapped and compressed, as described above, the balloon wrapping tool 10 may be slid off the distal end of the catheter 30 and discarded, or can be slid back down the shaft and resecured at the proximal hub. The position of catheter 30 in FIG. 1 shows the balloon 34 successfully wrapped and the balloon wrapping tool 10 slid off the distal end of the catheter 30.

FIG. 2 is a cross-sectional side view of the balloon wrapping tool 10 of FIG. 1, taken along line 2—2. The flap forming section 12 has a flap forming bore 18, the flap wrapping section 14 has a flap wrapping bore 37, and the flap compression section 16 has a flap compression bore 39. The flap forming bore 18, flap wrapping bore 37 and the flap compression bore 39 are preferably axially aligned to allow easy insertion of the balloon 20 therethrough. The size and shape of the proximal end of the flap wrapping bore 37 preferably substantially matches the size and shape of the distal end of the flap forming bore 18. Likewise, the size and shape of the distal end of the flap wrapping bore 37 substantially matches the size and shape of the proximal end of the flap compression bore 39. Thus, the flap wrapping bore provides a transition from the flap forming bore 18 to the flap compression bore 39. The flap compression bore 39 is preferably dimensioned to be near the desired profile of the wrapped balloon 20, but may have a slight inward taper toward the distal end to provide the lowest possible profile to the distal end of the balloon.

FIG. 3 is a cross-sectional view of the balloon wrapping tool 10 of FIG. 2, taken along line 3—3, and showing the cross-section of the flap forming section 12. In this embodiment, the flap forming bore 18 is substantially triangular in shape with three arcuate shaped side surfaces 40a, 40b and 40c. When the balloon 20 is inflated and subsequently deflated in the flap forming bore 18, the balloon will have three equally spaced flaps.

FIG. 4 is a cross-sectional view of the balloon wrapping tool of FIG. 2, taken along line 4—4, and showing the cross-section of the proximal portion of the flap wrapping section 14. As indicated above, the size and shape of the proximal end of the flap wrapping bore 37 substantially matches the size and shape of the distal end of the flap forming bore 18. Thus, at line 4—4, the flap wrapping bore 37 has transitioned from the shape shown in FIG. 3 to more of a triangle shape. FIG. 5 showing a cross-section of a distal portion of the flap wrapping section 14, and specifically along line 5—5. The size and shape of the distal end of the flap wrapping section 14 preferably substantially matches the size and shape of the proximal end of the flap compression bore 39. Thus, at line 5—5, the flap wrapping bore 37 has transitioned from the shape shown in FIG. 4 to more of a rounded-off triangle shape.

FIG. 6 is a cross-sectional view of the balloon wrapping tool of FIG. 2, taken along line 6—6, showing the cross-section of the balloon compression bore 39. The balloon compression bore 39 is preferably substantially round and has a diameter that is near the desired wrapped balloon profile.

FIG. 7 is a cross-sectional view of a flap forming section of another illustrative balloon wrapping tool. In this embodiment, the flap forming section has a flap forming bore 50 that is substantially X-shaped with four arcuate shaped side surfaces 52a, 52b, 52c and 52d. When the balloon 20 is inflated and subsequently deflated in the flap forming bore 50, the balloon will have four equally spaced flaps.

FIG. 8 is a cross-sectional view of the flap forming section of yet another illustrative balloon wrapping tool. In this embodiment, the flap forming section has a flap forming bore 54 that is substantially star-shaped having five inwardly extending grooves 56a, 56b, 56c, 56d and 56e. When the balloon 20 is inflated and subsequently deflated in the flap forming bore 54, the balloon will have five equally spaced flaps.

FIG. 9 is a cross-sectional view of the flap forming section of yet another illustrative balloon wrapping tool including three movable protrusions. In this embodiment, the flap forming section includes a flap forming bore 60 with three slots for receiving the spaced elongate protrusions 62a, 62b and 62c. Before the balloon is inserted into the flap forming bore 60, the elongate protrusions 62a, 62b and 62c are placed in an outward position, as shown in FIG. 9. After the balloon is inserted into the flap forming bore 60, the elongate protrusions 62a, 62b and 62c are moved inward toward the balloon, as shown in FIG. 10. Thereafter, the balloon is inflated and subsequently deflated to form three equally spaced flaps. The elongate protrusions 62a, 62b and 62c may then be moved back to the outward position shown in FIG. 9.

FIG. 11 is a perspective view of a another illustrative balloon wrapping tool in accordance with the present invention. The balloon wrapping tool of this embodiment also has a flap forming section 100, a flap wrapping section 102 and a flap compression section 104. The flap forming section 100 and flap compression section 104 are similar to that shown in FIG. 1. However, the flap wrapping section 102 has a spiral shape to help fold the balloon flaps in a single direction around the catheter.

FIG. 12 is a cross-sectional side view of the balloon wrapping tool of FIG. 11, taken along line 12—12, showing the flap forming section 100, flap wrapping section 102 and the flap compression section 104. The shape of the flap wrapping section 102, which substantially matches the shape of the flap forming section 100 at its proximal end, is gradually rotated radially about the central axis of the balloon wrapping tool. At the same time, the dimensions of the flap wrapping bore are reduced to match the size and shape of the balloon compression bore at its distal end. This change in shape urges the flaps of the balloon to wrap around the catheter in a single direction when the balloon is inserted therethrough.

FIG. 13 is a cross-sectional view of the balloon wrapping tool of FIG. 12, taken along line 13—13. The balloon is shown having three flaps 110a, 110b and 110c each positioned within one of the three regions 114, 116 and 118. The flaps are shown just beginning to fold over the catheter 112, all in the same direction. As the balloon is advanced further into the flap wrapping section 102, as shown more fully in FIG. 14, the three flaps 110a, 110b and 110c are further folded over the catheter 112. The three regions 114, 116 and 118 are shown as rotated to the left. In these figures, the balloon wrapping tool has not been rotated. Rather the shape of the flap wrapping section 102 has changed. As the balloon is advanced further into the flap wrapping section 102, as shown more fully in FIG. 15, the three flaps 110a, 110b and 110c are further folded over the catheter 112. Finally, FIG. 16 shows the balloon advanced into the flap compression section 104. In the flap compression section, the three flaps 110a, 110b and 110c are fully folded over the catheter 112 and ready for compression.

FIG. 17 is a cross-sectional side view of a balloon wrapping tool that includes a lubricious coating on the inside surface thereof. In some cases, the friction between the balloon and the balloon wrapping tool may be significant, particularly when advancing the balloon into the compression section. Thus, it is contemplated that a lubricious layer 130 may be provided on the surfaces of the flap forming bore, the flap wrapping bore and/or the flap compression bore. Alternatively, or in addition to, the surfaces of the flap forming bore, the flap wrapping bore and/or the flap compression bore may include a pattern of projections to reduce the frictional forces, such as the dimple pattern shown in FIG. 18.

FIG. 19 is a partial cross-sectional side view of the compression section of another illustrative balloon wrapping tool. In this embodiment, the compression section includes one or more slits 150 along a portion thereof The slit allows the compression section to assume a reduced diameter when compressed by a compression tool 152. Preferably, the compression tool has an inner bore 154 that reduces in diameter toward the distal end 158 thereof After the balloon is positioned in the compression section, the proximal end 156 of the compression tool 152 may be slid over the compression section of the balloon wrapping tool as shown. Because the diameter of the inner bore 154 reduces toward the distal end 158 thereof, the balloon becomes further compressed as the compression tool 152 is advanced proximally. The compression tool 152 may be advanced proximally until the desired balloon profile is achieved.

FIG. 20 is a perspective view of yet another illustrative balloon wrapping tool in accordance with the present invention. In this embodiment, the balloon wrapping tool 160 includes, from the proximal end to the distal end, a flap forming section 162, a first flap wrapping section 164, a flap compression section 166 and a second flap wrapping section 168. This illustrative embodiment may be particularly useful for wrapping and/or rewrapping the balloon of a single operator exchange type device. In a single operator exchange type device, the guide wire typically only extends through a short guide wire lumen that extends through the distal end of the catheter. The guide wire typically enters a guide wire port 170 that is located proximate the balloon, and extends out the distal end of the catheter. Typically, the guide wire provides significant column support for the catheter shaft. Since the guide wire only extends through a relatively short distal portion of a single operator exchange type device, the guide wire does not provide significant column support to the catheter shaft that is proximal to the guide wire port 170.

To properly form the balloon, the flap forming section 162 of the balloon wrapping tool 160 preferably has a length that is at least as long as the balloon. When the balloon is positioned within the flap forming section 162, the operator or physician will likely be able to grasp the catheter shaft at or distal of the proximal guide wire port 170. For some single-operator exchange type catheters, the operator will also be able to grasp the catheter shaft near the proximal guide wire port 170 even as the balloon is advanced into the flap wrapping section 164. However, as the balloon is advanced into the flap compression section 166, the operator may not be able to grasp the catheter shaft sufficiently close to the proximal guide 15 wire port 170, and the catheter may lack the column support to allow the balloon to be pushed into the compression section 166 without kinking. Because of the lack of column support, and the inability of the operator or physician to grasp the catheter sufficiently close to the proximal guide wire port, it may not be possible to advance the balloon of a single operator exchange type device into the flap wrapping section 166 and/or the flap compression section, as described above.

Accordingly, after the balloon is inflated and deflated in the flap forming section 162, the balloon may be withdrawn from the balloon wrapping tool 160, as shown by arrows 176. The balloon may then be inserted into the flap wrapping section 168, which in this embodiment, is located on the opposite side of the compression section 166 from the balloon forming section 162. This is indicated by arrows 177. Since no flap forming section is provided adjacent to the flap wrapping section 168, the operator or physician may grasp the catheter shaft near the proximal guide wire port 170, and provide the needed column support to advance the balloon into the flap wrapping section 168 and flap compression section 166. Thus, the operator or physician may advance the balloon into the flap wrapping section 168 and the flap compression section 166 to complete the forming, wrapping and compression of the balloon.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A method for rewrapping an inflatable balloon of a balloon type catheter after the balloon has been inflated during a medical procedure, the method comprising the steps of:

inflating the balloon in a flap forming bore of a balloon rewrapping tool, wherein the flap forming bore is shaped to produce at least two flaps in the balloon when the balloon is inflated and subsequently deflated therein;

deflating the balloon;

advancing the deflated balloon into a flap wrapping bore of the balloon rewrapping tool, wherein the flap wrapping bore is shaped to wrap the at least two flaps around the catheter as the deflated balloon is advanced therethrough, thereby resulting in a wrapped balloon.

2. A method according to claim 1 further comprising the step of:

advancing the wrapped balloon into a flap compression bore of the balloon rewrapping tool.

3. A method according to claim 2 further comprising the steps of:

inflating the wrapped balloon while in the flap compression bore;

deflating the wrapped balloon while in the flap compression bore; and removing the wrapped balloon from the flap compression bore.

4. A method for wrapping an inflatable balloon of a balloon type catheter using a balloon wrapping tool, wherein the balloon wrapping tool has a flap forming bore, a flap wrapping bore and a flap compression bore formed therein, the method comprising the steps of:

inserting the balloon into the flap forming bore, the flap forming bore having a shape that produces at least two flaps in the balloon when the balloon is inflated and subsequently deflated therein;

inflating the balloon;

deflating the balloon, thereby producing the at least two flaps in the deflated balloon; and advancing the deflated balloon into the flap wrapping bore, wherein the flap wrapping bore is shaped to wrap the at least two flaps of the balloon onto the catheter as the deflated balloon is advanced therethrough.

5. A method according to claim 4 further comprising the steps of:

advancing the deflated balloon into the flap compression bore;

inflating the balloon in the flap compression bore;

deflating the balloon in the flap compression bore; and removing the balloon from the balloon wrapping tool.

* * * * *

UNITED STATES PATENT AND TRADEMARK OFFICE
CERTIFICATE OF CORRECTION

PATENT NO.    : 6,623,689 B2
DATED         : September 23, 2003
INVENTOR(S)   : Richard J. Traxler et al.

It is certified that error appears in the above-identified patent and that said Letters Patent is hereby corrected as shown below:

Column 10,
Line 7, after "proximal guide" and before "wire port", delete "15".

Signed and Sealed this

Twenty-ninth Day of June, 2004

JON W. DUDAS
*Acting Director of the United States Patent and Trademark Office*